US006121246A

United States Patent [19]
Isner

[11] Patent Number: 6,121,246
[45] Date of Patent: *Sep. 19, 2000

[54] METHOD FOR TREATING ISCHEMIC TISSUE

[75] Inventor: Jeffrey M. Isner, Weston, Mass.

[73] Assignee: St. Elizabeth's Medical Center of Boston, Inc., Boston, Mass.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/545,998

[22] Filed: Oct. 20, 1995

[51] Int. Cl.$^7$ .......................... A01N 43/04; A61K 31/70; C12N 15/63; C12N 15/00

[52] U.S. Cl. .......................... 514/44; 435/455; 435/320.1; 435/69.1; 435/69.7; 435/69.8

[58] Field of Search .......................... 514/44; 435/320.1, 435/69.1, 172.3, 69.7, 69.8, 455

[56] References Cited

U.S. PATENT DOCUMENTS

| | | | |
|---|---|---|---|
| 5,580,859 | 12/1996 | Felgner et al. | |
| 5,589,466 | 12/1996 | Felgner et al. | |
| 5,593,972 | 1/1997 | Weiner et al. | |
| 5,661,133 | 8/1997 | Leiden et al. | 514/44 |
| 5,693,622 | 12/1997 | Wolff et al. | 514/44 |
| 5,792,453 | 8/1998 | Hammond et al. | 424/93.21 |

FOREIGN PATENT DOCUMENTS

| | | |
|---|---|---|
| WO 90/11092 | 10/1990 | WIPO. |
| WO 93/00051 | 1/1993 | WIPO. |
| WO 93/00052 | 1/1993 | WIPO. |
| WO 94/11506 | 5/1994 | WIPO. |

OTHER PUBLICATIONS

Baumgartner I. et al. "Constitutive expression of phVEGF$_{165}$ after intramuscular gene transfer promotes collateral vessel development in patients with critical limb ischemia", Circulation 97: 1114–1123 (1998).
Friesel, R. E. et al. "Molecular mechanisms of angiogenesis: fibroblast growth factor signal transduction", FASEB J. 9: 919–925 (1995).
Henry, T. D. et al. "Double blind, placebo controlled trial of recombinant human vascular enothelial growth factor—the VIVA trial", J. Am. Coll. Cardiol. 874–4 (1999).
Young, E. "No significant differences between VEGF, placebo", Cardiology Today, Apr. 1999.
Isner, J. M. et al. "Clinical evidence of angiogenesis after arterial gene transfer of phVEGF$_{165}$ in patient with ischaemic limb", The Lancet 438: 370–374 (1996).
Jiao, S. et al. "Direct gene transfer into nonhuman primate myofibers in vivo", Hum. Gene Ther. 3: 21–33 (1992).
Marshall, D. J. et al. "Recent advances in skeletal–muscle–based gene therapy", Curr. Opin. Gen. Dev. 8: 360–365 (1998).
Nabel, E. G. et al. "Recombinant fibroblast growth factor–1 promotes intimal hyperplasia and angiogenesis in arteries in vivo", Nature 342: 844–846 (1993).
Jaye, M. et al. "Expression of acidic fibroblast growth factor cDNA confers growth advantage and tumorigenesis to Swiss 3T3 cells", EMBO J. 7:963–969 (1988).
Sambrook, J. et al. "Molecular Cloning, A Laboratory Manual", Cold Spring Harbor Laboratory Press, 1989, pp. 17.31–17.33.
Minchenko et al., Laboratory Investigation, vol. 71, No. 3, pp. 374–379, Sep. 1994.
Feldman et al., Fundam. Clin. Pharmacol., vol. 9, pp. 8–16, 1995.
Simons & Ware, Nature Medicine, vol. 2, pp. 519–520, May 1996.
Isner et al., Circulation, vol. 91, pp. 2687–2692, 19
Mulligan, Science, vol. 260, pp. 926–930, May
Afione et al., Clin. Pharmacokinet., vol. 28, pp. 181–189, 1995.
Riessen & Isner, Journal Am. Coll. Cardiol., vol. 23, pp. 1234–1244, 1994.
Marshall, Science, vol. 269, pp. 1050–1055, Aug. 25, 1995.
Coghlan, Focus, vol. 145, pp. 14–15, Nov. 25, 1995.
Brown, The Washington Post, "News Media Researchers 'Oversold' Gene Therapy . . . Says", Dec. 8, 1995.
Setoguchi et al., Blood, vol. 84, pp. 2946–2953, Nov. 1, 1994.
Nabel et al., Nature, vol. 362, pp. 844–846, Apr. 29, 1993.
Symes et al., Current Opinion in Lipidology, vol. 5, pp. 305–312, Aug. 1994.
Hockel, et al., Arch. Surg., vol. 128 pp. 423–429 (1993).
Baffour, et al., J. Vasc. Surg., 16:181–91, 1992.
Pu, et al., J. Surg. Res., 54:575–83, 1993.
Takeshita, et al., J. Clin. Invest., 93:662–70, 1994.
Jorgensen, et al., Lancet, 1:1106–1108, 1989.
Wolinsky, et al., J. Am. Coll. Cardio., 15:475–485, 1990.
Isner, et al., Circulation, 88:1534–1557, 1993.
Wolff, et al., Science, 247:1465–1468, 1990.
Miller, Nature, 357:455–60, 1992.
Folkman, et al., Science, 235:442–447, 1987.

(List continued on next page.)

*Primary Examiner*—Jasemine Chambers
*Assistant Examiner*—Jill Martin
*Attorney, Agent, or Firm*—Dike, Bronstein, Roberts & Cushman, LLP; David G. Conlin

[57] ABSTRACT

The present invention provides a method for treating ischemic tissue in a mammal which comprises injecting said tissue with an effective amount of a nucleic acid capable of expressing an angiogenic protein. The method of the present invention may be used to treat any ischemic tissue, i.e., a tissue having a deficiency in blood as the result of an ischemic disease. Such tissues can include, for example, muscle, brain, kidney and lung. Ischemic diseases include, for example, cerebrovascular ischemia, renal ischemia, pulmonary ischemia, limb ischemia, ischemic cardiomyopathy and myocardial ischemia.

30 Claims, 6 Drawing Sheets

OTHER PUBLICATIONS

Klagsbrun, et al., *Annu. Rev. Physiol.,* 53:217–239, 1991.
Folkman, et al., *J. Biol. Chem.,*267:10931–10934, 1992.
Symes, et al., *Current Opinion in Lipidology,* 5:305–312, 1994.
Pu, et al., *Circulation,* 88:208–215, 1993.
Ferrara, et al., *Biochem. Biophys. Res. Commun.,* 161:851–855, 1989.
Keck, et al., *Science,* 246:1309–1342, 1989.
Connolly, et al., *J. Biol. Chem.,* 264:20017–20024, 1989.
Conn, et al., *Proc. Natl. Acad. Sci., USA,* 87:1323–1327, 1990.
Shen, et al., *Blood,* 81:2767–2773, 1993.
Clauss, et al., *J. Exp. Med.,* 172:1535–1545, 1990.
Connolly, et al., *J. Clin. Invest.,* 84:1470–1478, 1989.
Nabel, et al., *Nature,* 362:844, 1993.
Davis, et al., *Hum. Gene Ther.,* 4:151, 1993.
Wolff, et al., *Biotechniques,* vol. 11, No. 4 474–485, 1991.
Acsadi, et al., *The New Biologist,* vol. 3, No. 1, 71–81, 1991.

J. Isner and L. Feldman, The Lancet, vol. 344 (1994), pp. 1653–1654.

R. Sanders Williams, Amer. J. of Med. Sci., vol. 306, No. 2 (1993) pp. 129–136.

Mesri, et al., Cir. Res., vol. 76, No. 2 (1995), pp. 161–167.

Fan, et al., TiPS, vol. 16 (1995) pp. 57–66.

Isner, et al., Circulation, vol. 91, No. 11 (1995), pp. 2687–2692.

Supplement to Circulation, vol. 88, No. 4, Part 2 (1993) Abstracts from the 66th Scientific Sessions (pp. I–475–I476.

Capogrossi, M.C, "Gene Therapy of Coronary Artery Disease" Grant Abstract AG00811–01 (1994).

Capogrossi, M.C, "Gene Therapy of Coronary Artery Disease" Grant Abstract AG00811–02 (1995).

Isner, J.M., "Therapeutic Angiogenesis in Vascular Medicine" Grant Abstract HL–53354–01 (1995).

FIG. IA
FIG. IB

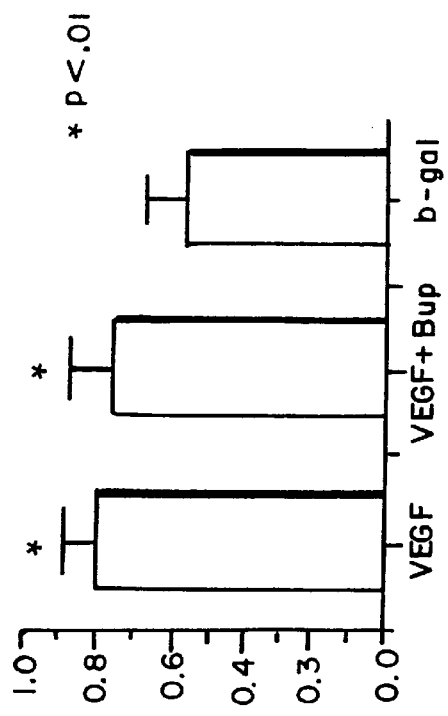
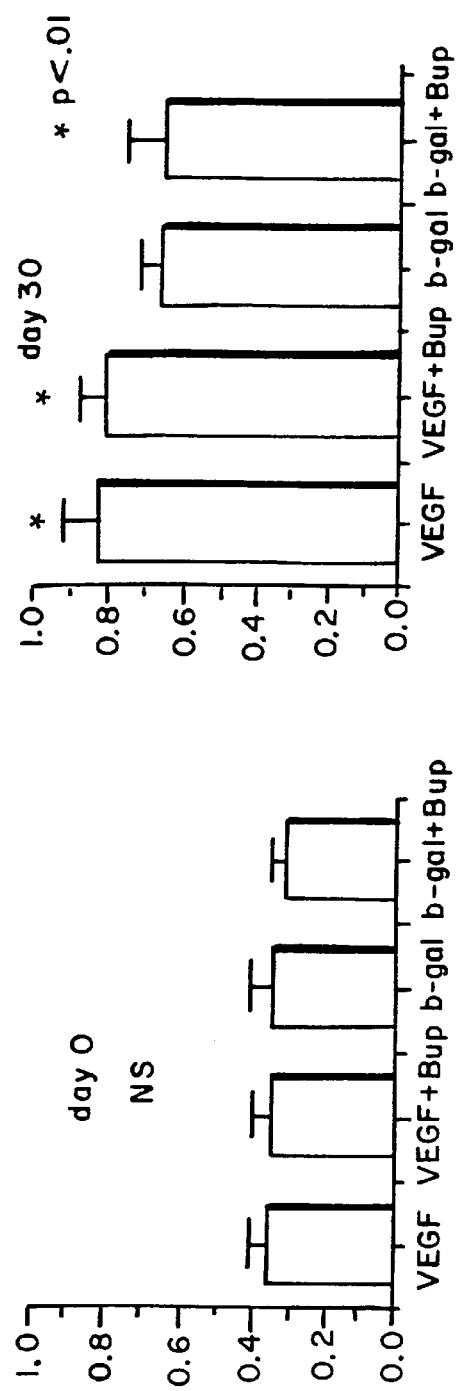
FIG. 5A
FIG. 5B

METHOD FOR TREATING ISCHEMIC TISSUE

FIELD OF THE INVENTION

The present invention is directed to a method for enhancing blood vessel development in ischemic tissues.

BACKGROUND OF THE INVENTION

The therapeutic implications of angiogenic growth factors were first described by Folkman and colleagues over two decades ago (Folkman, *N Engl J Med,* 285:1182–1186 (1971)). Recent investigations have established the feasibility of using recombinant angiogenic growth factors, such as fibroblast growth factor (FGF) family (Yanagisawa-Miwa, et al., *Science,* 257:1401–1403 (1992) and Baffour, et al., *J Vasc Surg,* 16:181–91 (1992)), endothelial cell growth factor (ECGF)(Pu, et al., *J Surg Res,* 54:575–83 (1993)), and more recently, vascular endothelial growth factor (VEGF) to expedite and/or augment collateral artery development in animal models of myocardial and hindlimb ischemia (Takeshita, et al., *Circulation,* 90:228–234 (1994) and Takeshita, et al., *J Clin Invest,* 93:662–70 (1994)). In studies with recombinant angiogenic growth factors, intra-muscular administration of the growth factor was repeated over a range of 10 to 14 days. Thus, one major limitation of recombinant protein therapy is its potential requirement to maintain an optimally high and local concentration over time.

Gene delivery systems employed to date have been characterized by two principal components: a macro delivery device designed to deliver the DNA/carrier mixture to the appropriate segment of the vessel, and microdelivery vehicles, such as liposomes, utilized to promote transmembrane entry of DNA into the cells of the arterial wall. Macrodelivery has typically been achieved using one of two catheters initially developed for local drug delivery: a double-balloon catheter, intended to localize a serum-free arterial segment into which the carrier/DNA mixture can be injected, or a porous-balloon catheter, designed to inject gene solutions into the arterial wall under pressure. Jorgensen et al., *Lancet* 1:1106–1108 (1989); Wolinsky, et al., *J. Am. Coll. Cardiol.,* 15:475–485 (1990); March et al., *Cardio Intervention,* 2:11–26 (1992)); WO93/00051 and WO93/00052.

Double balloon catheters are catheters which have balloons which, when inflated within an artery, leave a space between the balloons. The prior efforts have involved infusing DNA-containing material between the balloons, allowing the DNA material to sit for a period of time to allow transfer to the cells, and then deflating the balloons, allowing the remaining genetic material to flush down the artery. Perforated balloons are balloons which have small holes in them, typically formed by lasers. In use, fluid containing the genetic material is expelled through the holes in the balloons and into contact with the endothelial cells in the artery. These gene delivery systems however, have been compromised by issues relating to efficacy and/or safety.

Certain liabilities, however, inherent in the use of double-balloon and porous balloon catheters have been identified. For example, neither double-balloon nor porous balloon catheters can be used to perform the angioplasty itself. Thus, in those applications requiring both angioplasty and drug delivery, e.g., to inhibit restenosis, two procedures must be preformed. Additionally, the double balloon typically requires long incubation times of 20–30 min., while the high-velocity jets responsible for transmural drug delivery from the porous balloon catheter have been associated with arterial perforation and/or extensive inflammatory infiltration (Wolinsky, et al., supra).

Recently, the feasibility of intra-arterial gene therapy for treatment of ischemia was demonstrated in a rabbit model with VEGF using another gene delivery system, a Hydrogel-coated angioplasty balloon. Successful transfer and sustained expression of the VEGF gene in the vessel wall subsequently augmented neovascularization in the ischemic limb (Takeshita, et al., *Proc Natl Acad Sci USA* (In Press)). However, alternative methods for inducing angiogenesis are still desirable for a number of reasons. First, use of catheter based gene delivery systems may bring out unpredictable abrupt closure or severe damage at the site of ballooning. The consequence may be more serious if the damaged artery is the major donor of the present collaterals or the only patent vessel supplying ischemic tissue. Second, it may be difficult to deliver a catheter to the distal lesion especially in cases of diffuse vascular disease. Finally, despite major advances in both surgical and percutaneous revascularization techniques, limb salvage and relief of ischemic pain cannot be achieved in many patients with diffuse peripheral vascular disease. Isner et al., *Circulation* 88:1534–1557 (1993)).

Striated animal muscle has been shown to take up and express injected foreign marker genes transferred in the form of plasmid DNA (Wolff, et al., *Science,* 247:1465–1468 (1990)). Therapeutic gene transfection in the form of naked plasmid DNA injected directly into muscles has advantages over techniques using viral vectors and catheter based delivery systems. Mainly, it is free from immunological reactions associated with viral proteins (Miller, *Nature,* 357:455–60 (1992)), and avoids possible vascular injuries due to catheter delivery or ballooning procedures. However, direct gene transfer is considered to have insufficient expression to be considered for use in human gene therapy trials (Wolff, et al., supra, and Jiao, et al., *Hum Gene Ther,* 3:21–33 (1992)).

SUMMARY OF THE INVENTION

It has now been discovered that surprisingly nucleic acid (DNA or RNA) capable of expressing an angiogenic protein (a protein capable of inducing angiogenesis, i.e., the formation of new blood vessels), when injected into ischemic tissue, induces angiogenesis, providing the ischemic tissue with increased blood vessels. This allows for the treatment of ischemic tissue associated with ischemic diseases, while avoiding the use of other gene delivery systems.

The present invention provides a method for treating ischemic tissue in a mammal which comprises injecting said tissue with an effective amount of a nucleic acid capable of expressing an angiogenic protein.

The method of the present invention may be used to treat any ischemic tissue, i.e., a tissue having a deficiency in blood as the result of an ischemic disease. Such tissues can include, for example, muscle, brain, kidney and lung. Ischemic diseases include, for example, cerebrovascular ischemia, renal ischemia, pulmonary ischemia, limb ischemia, ischemic cardiomyopathy and myocardial ischemia.

The ischemic tissue may be injected with the nucleic acid by any injection means. One preferred means is a hypodermic needle. Other means include an externally applied local injection apparatus, such as that used to inject antigens for allergy testing; or a transcutaneous "patch" capable of delivery to subcutaneous muscle. The nucleic acid may be injected at more than one site in the ischemic tissue. If necessary, the nucleic acid may be reinjected to provide additional expression of the angiogenic protein.

The method of the present invention does not require a microdelivery vehicle such as cationic liposomes and adenoviral vectors, however, the nucleic acid may be carried by such vehicles. Nucleic acid encoding different angiogenic proteins may be used separately or simultaneously.

As used herein the term "angiogenic protein" means any protein, polypeptide, mutein or portion that is capable of, directly or indirectly, inducing the formation of new blood vessels. Such proteins include, for example, acidic and basic fibroblast growth factors (aFGF and bFGF), vascular endothelial growth factor (VEGF), epidermal growth factor (EGF), transforming growth factor α and β (TGF-α and TFG-β), platelet-derived endothelial growth factor (PD-ECGF), platelet-derived growth factor (PDGF), tumor necrosis factor α (TNF-α), hepatocyte growth factor (HGF), insulin like growth factor (IGF), erythropoietin, colony stimulating factor (CSF), macrophage-CSF (M-CSF), granulocyte/macrophage CSF (GM-CSF) and nitric oxidesynthase (NOS). Preferably, the angiogenic protein contains a secretory signal sequence allowing for secretion of the protein. VEGF is a preferred protein.

The term "effective amount" means a sufficient amount of nucleic acid delivered to the cells of the ischemic tissue to produce an adequate level of the angiogenic protein, i.e., levels capable of inducing angiogenesis. Thus, the important aspect is the level of protein expressed. Accordingly, one can use multiple transcripts or one can have the gene under the control of a promoter that will result in high levels of expression. In an alternative embodiment, the gene would be under the control of a factor that results in extremely high levels of expression, e.g., tat and the corresponding tar element.

BRIEF DESCRIPTION OF THE DRAWINGS

FIGS. 1A and 1B sets forth representative angiograms recorded from both control (1B) and VEGF-treated (1A) animals at day 30.

FIGS. 5A–5B illustrates reduction of the hemodynamic deficit in the ischemic limb following intramuscular VEGF-transfection as confirmed by measurement of calf blood pressure.

DETAILED DESCRIPTION OF THE INVENTION

Figure 2A:
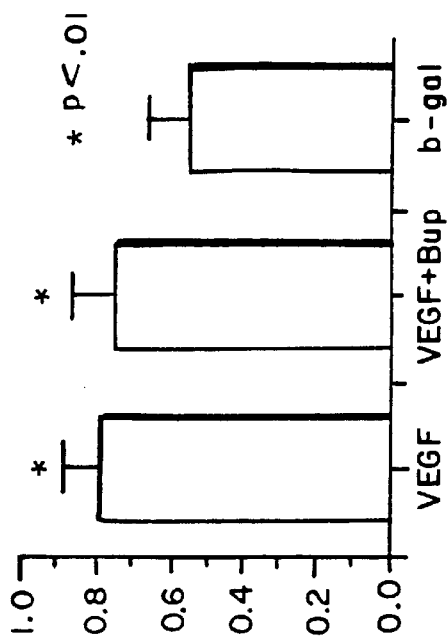
FIGS. 2A–2B illustrates the angiographic score seen in the acute and chronic ischemia models.

The present invention provides a method for treating ischemic tissue in a mammal which comprises injecting said tissue with an effective amount of a nucleic acid encoding an angiogenic protein operably linked to a promoter (nucleic acid cassette) to result in expression of the protein when delivered to the ischemic tissue. The resulting expression of the angiogenic protein results in increased blood vessel formation throughout the ischemic tissue. The methods of the present invention may be used to treat the ischemic tissue that results from ischemic diseases such as cerebrovascular ischemia, renal ischemia, pulmonary ischemia, limb ischemia, ischemic cardiomyopathy and myocardial ischemia.

The nucleic acid may be any nucleic acid (DNA or RNA) including genomic DNA, cDNA and mRNA, encoding an angiogenic protein i.e., a protein, polypeptide, mutein or portion that is capable of inducing the formation of new blood vessels. Such proteins include, for example, any protein, polypeptide, mutein or portion thereof that is capable of inducing, either directly or indirectly, the formation of new blood vessels. Folkman, et al., *Science*, 235:442–447 (1987). These include, for example, acidic and basic fibroblast growth factors (aFGF and bFGF), vascular endothelial growth factor (VEGF), epidermal growth factor (EGF), transforming growth factor α and β (TGF-α and TGF-β), platelet-derived endothelial cell growth factor (PD-ECGF), platelet-derived growth factor (PDGF) itself, tumor necrosis factor α (TNF-α), hepatocyte growth factor (HGF), insulin like growth factor (IGF) erythropoietin, colony stimulating factor (CSF), macrophage-CSF (M-CSF), granulocyte/macrophage CSF (GM-CSF) and nitric oxide synthase (NOS). See, Klagsbrun, et al., *Annu. Rev. Physiol.*, 53:217–239 (1991); Folkman, et al., *J. Biol. Chem.*, 267:10931–10934 (1992) and Symes, et al., *Current Opinion in Lipidology*, 5:305–312 (1994). Muteins or fragments of an angiogenic protein may be used as long as they induce or promote the formation of new blood vessels.

Recent investigations have established the feasibility of using recombinant formulations of such angiogenic growth factors to expedite and/or augment collateral artery development in animal models of myocardial and hindlimb ischemia. See, Baffour, et al., supra (bFGF); Pu, et al, *Circulation*, 88:208–215 (1993) (aFGF); Yanagisawa-Miwa, et al., supra (bFGF); Ferrara, et al., *Biochem. Biophys. Res. Commun.*, 161:851–855 (1989) (VEGF).

In addition, therapeutic angiogenesis has been achieved in the same or closely related models following administration of recombinant endothelial cell growth factor (ECGF) (Pu, et al., *Circulation*, 88:208–215 (1993)) and VEGF (Takeshita, et al., *Circulation*, 90:228–234 (1994) supra). Previous studies, employing the animal model of chronic limb ischemia, demonstrated an efficacy of intra-muscular endothelial cell growth factor (ECGF) (Pu, et al., *Circulation*, 88:208–215 (1993)) or VEGF (Takeshita, et al., *Circulation*, 90:228–234 (1994) supra) administration.

VEGF was purified independently as a tumor-secreted factor that included vascular permeability by the Miles assay (Keck, et al, *Science*, 246:1309–1342 (1989) and Connolly, et al., *J. Biol. Chem.*, 264:20017– 20024 (1989)), and thus its alternate designation, vascular permeability factor (VPF). VEGF is a preferred angiogenic protein. Two features distinguish VEGF from other heparin-binding, angiogenic growth factors. First, the $NH_2$ terminus of VEGF is preceded by a typical signal sequence; therefore, unlike bFGF, VEGF can be secreted by intact cells. Second, its high-affinity binding sites, shown to include the tyrosine kinase receptors Flt-1 and Flt-1/KDR are present on endothelial cells. Ferrara, et al., supra, and Conn, et al., *Proc Natl Acad Sci USA*, 87:1323–1327 (1990). (Interaction of VEGF with lower affinity binding sites has been shown to induce mononuclear phagocyte chemotaxis). Shen, et al., *Blood*, 81:2767–2773 (1993) and Clauss, et al., *J. Exp. Med.*, 172:1535–1545 (1990). The DNA encoding VEGF is disclosed in U.S. Pat. No. 5,332,671, the disclosure of which is herein incorporated by reference.

Evidence that VEGF stimulates angiogenesis in vivo had been developed in experiments performed on rat and rabbit cornea (Levy, et al., *Growth Factors,* 2:9–19 (1989) and Connolly, et al., *J. Clin. Invest.,* 84:1470–1478 (1989)), the chorioallantoic membrane (Ferrara, et al., supra), and the rabbit bone graft model. Connolly, et al., *J. Clin. Invest.,* 84:1470–1478 (1989) supra.

Preferably, the angiogenic protein contains a secretory signal sequence that facilitates secretion of the protein. Angiogenic proteins having native signal sequences, e.g., VEGF, are preferred. Angiogenic proteins that do not have native signal sequences, e.g., bFGF, can be modified to contain such sequences using routine genetic manipulation techniques. See, Nabel et al., *Nature,* 362:844 (1993).

The nucleotide sequence of numerous angiogenic proteins, are readily available through a number of computer data bases, for example, GenBank, EMBL and Swiss-Prot. Using this information, a DNA segment encoding the desired protein may be chemically synthesized or, alternatively, such a DNA segment may be obtained using routine procedures in the art, e.g, PCR amplification.

To simplify the manipulation and handling of the nucleic acid encoding the protein, the nucleic acid is preferably inserted into a cassette where it is operably linked to a promoter. The promoter must be capable of driving expression of the protein in cells of the desired target tissue. The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., *Hum Gene Ther* 4:151 (1993)) and MMT promoters may also be used. Certain proteins can expressed using their native promoter. Other elements that can enhance expression can also be included such as an enhancer or a system that results in high levels of expression such as a tat gene and tar element. This cassette can then be inserted into a vector, e.g., a plasmid vector such as pUC118, pBR322, or other known plasmid vectors, that includes, for example, an *E. coli* origin of replication. See, Sambrook, et al., *Molecular Cloning: A Laboratory Manual,* Cold Spring Harbor Laboratory press, (1989). The plasmid vector may also include a selectable marker such as the β-lactamase gene for ampicillin resistance, provided that the marker polypeptide does not adversely effect the metabolism of the organism being treated. The cassette can also be bound to a nucleic acid binding moiety in a synthetic delivery system, such as the system disclosed in WO 95/22618.

If desired, the DNA may also be used with a microdelivery vehicle such as cationic liposomes and adenoviral vectors. For a review of the procedures for liposome preparation, targeting and delivery of contents, see Mannino and Gould-Fogerite, *BioTechniques,* 6:682 (1988). See also, Feigner and Holm, *Bethesda Res. Lab. Focus,* 11(2):21 (1989) and Maurer, R.A., *Bethesda Res. Lab. Focus,* 11(2):25 (1989).

Replication-defective recombinant adenoviral vectors, can be produced in accordance with known techniques. See, Quantin, et al., *Proc. Natl. Acad. Sci. USA,* 89:2581–2584 (1992); Stratford-Perricadet, et al., *J. Clin. Invest.,* 90:626–630 (1992); and Rosenfeld, et al., *Cell,* 68:143–155 (1992).

The effective dose of the nucleic acid will be a function of the particular expressed protein, the target tissue, the patient and his or her clinical condition. Effective amount of DNA are between about 1 and 4000 µg, more preferably about 1000 and 2000, most preferably between about 2000 and 4000.

In certain situations, it may be desirable to use nucleic acids encoding two or more different proteins in order to optimize the therapeutic outcome. For example, DNA encoding two angiogenic proteins, e.g., VEGF and bFGF, can be used, and provides an improvement over the use of bFGF alone. Or an angiogenic factor can be combined with other genes or their encoded gene products to enhance the activity of targeted cells, while simultaneously inducing angiogenesis, including, for example, nitric oxide synthase, L-arginine, fibronectin, urokinase, plasminogen activator and heparin.

In order to facilitate injection, the nucleic acid is formulated with a pharmaceutically acceptable carrier. Examples of suitable carriers include, saline, albumin, dextrose and sterile water. The nucleic acid is injected into the ischemic tissue using standard injection techniques by use of, for example, a hypodermic needle. Hypodermic needle sizes between no. 29 to no. 16 are preferred.

The nucleic acid may also be injected by an externally applied local injection apparatus, such as that used to inject antigens for allergy testing; or a transcutaneous "patch" capable of delivery to subcutaneous muscle.

The nucleic acid can be injected at multiple sites throughout the ischemic tissue.

Once injected, the nucleic acid capable of expressing the desired angiogenic protein is taken up and expressed by the cells of the tissue. Because the vectors containing the nucleic acid of interest are not normally incorporated into the genome of the cells, expression of the protein of interest takes place for only a limited time. Typically, the angiogenic protein is only expressed in therapeutic levels for about two days to several weeks, preferably for about 1–2 weeks. Reinjection of the DNA can be utilized to provide additional periods of expression of the angiogenic protein. If desired, use of a retrovirus vector to incorporate the heterologous DNA into the genome of the cells will increase the length of time during which the therapeutic polypeptide is expressed, from several weeks to indefinitely.

Expression of the angiogenic protein and its secretion from the tissue cells induces angiogenesis, allowing for the treatment of ischemia and thus diseases such as limb ischemia, cerebrovascular ischemia, renal ischemia, pulmonary ischemia, ischemic cardiomyopathy and myocardial ischemia.

All documents mentioned herein are incorporated by reference herein in their entirety.

The present invention is further illustrated by the following examples. These examples are provided to aid in the understanding of the invention and are not construed as a limitation thereof.

EXAMPLE 1

Induction of Angiogenesis in Ischemic Tissue By Direct Injection of DNA

Methods
Plasmids

Complementary DNA clones for recombinant human $VEFG_{165}$, isolated from cDNA libraries prepared from HL60 leukemia cells, were assembled into a simple eukaryotic expression plasmid that utilizes 736 bp cytomegalovirus promoter/enhancer to drive VEGF expression. Downstream from the VEGF cDNA is an SV40 polyadenylation sequence. Also included in this plasmid is a fragment containing the SV40 origin of replication that includes the 72 bp repeat, but this sequence is not functionally relevant (for autonomous replication) in the absence of SV40 T antigen. These fragments occur in the pUC118 vector which includes an *E. coli* origin of replication and the β-galactosidase gene for ampicillin resistance. The biological activity of $VEGF_{165}$ secreted from cells transfected with this construct ($phVEGF_{165}$) was previously confirmed by evidence that media conditioned by transfected human 293 cells promoted the proliferation of capillary cells (Leung, et al., *Science*, 246:1306–9 (1989)).

The plasmid pGSVLacZ (courtesy of Dr. Claire Bonnerot) containing a nuclear targeted β-galactosidase sequence coupled to the simian virus 40 early promoters (Bonnerot, et al., *Proc Natl Acad Sci, U.S.A.*, 84:6795–9 (1987)) was used for all the control transfection experiments.

Animal model

New Zealand white rabbits with operatively induced unilateral hindlimb vascular insufficiency, (Takeshita, et al., *Circulation*, 90:228–234 (1994) supra; Takeshita, et al., *J. Clin. Invest.* 93:662–70 (1994), supra; Pu, et al., *Circulation*, 88:208–215 (1993) supra, were used to model both acute and chronic ischemia. All protocols were approved by the Institutional Animal Care and Use Committee. The care of animals complied with the guidelines of the Canadian Council of Animal Care, the Principles of Laboratory Animal Care, and the Guide for the Care and Use of Laboratory Animals (NIH publication No. 80-23, revised 1985). Fifty-nine male New Zealand White rabbits (mean weight=3 kg) were anesthetized with ketamine (50 mg/kg) and xylazine (5 mg/kg). Through a longitudinal incision performed in a medial thigh, the femoral artery was dissected free along its entire length, as were all major branches of the femoral artery, including the inferior epigastric, deep femoral, lateral circumflex and superficial epigastric arteries. After further dissecting the popliteal and saphenous arteries distally, the external iliac artery as well as all of the above arteries were ligated. Finally, the femoral artery was completely excised from its proximal origin as a branch of the external iliac artery to the point distally where it bifurcates into the saphenous and popliteal arteries.

Intramuscular (IM) gene transfer

Acute limb ischemia. Twenty-eight rabbits were used to study the impact of IM gene transfer on acute hindlimb ischemia. Immediately following femoral artery excision as outlined above, five different sites in three major thigh muscles were injected directly with plasmid DNA using a 3 ml syringe and 27-gauge needle advanced through a small skin incision. For each injection, the tip of the needle was inserted into the adductor (2 sites), medial large (2 sites), and semimembranous muscles; care was taken, by directly visualizing each muscle during the injection, to avoid penetrating the muscle with the injectate. To the same end, the rate of injection was in each case slowed to approximately 5 sec so that injected solution would not leak through the epimysium. This injection technique was used to administer a total volume of 2.5 ml of a) a 500 µg $phVEGF_{165}$ in saline (n=8); b) 500 µg $phVEGF_{165}$ in 0.75% bupivacaine, previously shown to enhance transgene uptake by striated muscle (n=10) (Danko I, *Gene Therapy*, 1:114–21 (1994); or c) 500 µg pGSVLacZ encoding nuclear targeted β-galactosidase (n=10). After completing 5 injections (0.5 ml @ for each animal), the skin was then closed using 4.0 nylon.

Chronic limb ischemia. Thirty-one rabbits were used to study the effects of IM gene therapy for chronic hindlimb ischemia. The sole distinction between the chronic ischemia model and model of acute limb ischemia described above, is that an interval of 10 days was permitted for post-operative recovery, including development of endogenous collateral vessels. Accordingly, 10 days following femoral artery excision, the rabbits were returned to the catherization laboratory. After completing baseline physiological measurements described below, IM gene transfer using the identical technique described above was performed with a) 500 µg $phVEGF_{165}$ diluted in 2.5 ml of saline (n=8); b) 500 µg $phVEGF_{165}$ diluted in 0.75% bupivacaine (n=8); c) 500 µg of pGSVLacZ diluted in 2.5 ml of saline; or d) 500 µg of pGSVLacZ diluted in 2.5 ml of 0.75% bupivacaine (n=8). In each case, after completing 5 all injections, the skin was closed as above.

Anatomic Assessment

Selective angiography. Selective internal iliac arteriography was performed as previously described (Doucette, et al., *Circulation*, 85:1899–1911 (1992)). Briefly, a 3 Fr. infusion catheter (Tracker-18, Target Therapeutic, San Jose Calif.) was introduced into the common carotid artery and advanced to the internal iliac artery of the ischemic limb using 0.014 in. guidewire (Hi-Torque Floppy II, Advanced Cardiac System, San Diego, Calif.) under fluoroscopic guidance. The tip of catheter was positioned in the internal iliac artery at the level of the interspace between the seventh lumber and the first sacral vertebrae. Following intraarterial injection of nitroglycerin (0.25 mg, SoloPak Laboratories, Franklin Park, Ill.), a total of 5 ml of non-ionic contrast media (Isovue-370, Squibb Diagnostics, New Brunswick, N.J.) was then injected using an automated angiographic injector (Medrad, Pittsburgh, Pa.) programmed to reproducibly deliver a flow rate of 1 ml/sec. Serial images of the ischemic hindlimb were then recorded on 105-mm spot film at a rate of 1 film/sec for 10 sec.

Morphometric angiographic analysis of collateral vessel development was performed using a grid overlay comprised of 2.5 mm-diameter circles arranged in rows spaced 5 mm apart. This overlay was placed over the 4-sec angiogram recorded at the level of the medial thigh. A defined area was chosen in which the number of contrast-opacified arteries crossing over circles as well as the total number of circles encompassing the medial thigh area were counted in single blind fashion. An angiographic score was calculated for each film as the ratio of crossing opacified arteries divided by the total number of circles in the defined area of the ischemic thigh.

Capillary Density and Capillary/Myocyte Ratio. Anatomic evidence of collateral artery formation was further examined by measuring the number of capillaries in light microscopic sections taken from the ischemic hindlimbs (Takeshita, et al., *J. Clin. Invest.*, 93:662–70 (1994) supra). Tissue specimens were obtained as transverse sections from the adductor muscle, the major muscle of the medial thigh, of the ischemic limb at the time of sacrifice (day 30). Muscle samples were embedded in O.C.T. compound (Miles, Elkhart, Ind.) and snap-frozen in liquid nitrogen. Multiple frozen sections (5 µm in thickness) were then cut from each specimen on a cryostat (Miles), so that the muscle fibers were oriented in a transverse fashion. Tissue sections were stained for alkaline phosphatase using an indoxyl-tetrazolium method to detect capillary endothelial cells as previously described, and were then counterstained with eosin. A total of 20 different fields from one muscle section were randomly selected, and the number of capillaries was counted under a 20× objective to determine the capillary density (mean number of capillaries/$mm^2$). To ensure that analysis of capillary density was not overestimated due to muscle atrophy, or underestimated due to interstitial edema, capillaries identified at necropsy were also evaluated as a function of muscle fibers in the histologic section. The counting scheme used to compute the capillary/myocyte ratio was otherwise identical to that used to compute capillary density.

Physiologic Assessment

Calf blood pressure. Calf blood pressure was measured using a Doppler Flowmeter (Model 1059, Parks Medical Electronics, Aloha, Oreg.). The pulse of the posterior tibial artery was identified using a Doppler probe, and the systolic blood pressure in both limbs was determined using standard techniques (Takeshita, et al., *J. Clin Invest*, 93:662–70 (1994)). The calf blood pressure ratio was defined for each rabbit as the ratio of systolic pressure of the ischemic limb to that of the normal limb.

Intra-arterial Doppler guidewire measurement of flow velocity. Intra-arterial Doppler assessment was also performed on day 0 and 30 before selective internal iliac angiography. The tip of the 3 Fr. infusion catheter was positioned 2 cm above the aortic bifurcation. A total of 5 ml of non-ionic contrast media (Isovue-370, Squibb Diagnostics, New Brunswick, N.J.) was injected using an automated angiographic injector (Medrad, Pittsburgh, Pa.) at a rate of 1 ml/sec. Serial images of the aorta-iliac bifurcation were then recorded on 105-mm spot film at a rate of 1 film/sec for 5 sec. The 0.018 in. Doppler guidewire (Cardiometrics, Inc., Mountain View, Calif.) was then used to measure blood flow velocity as previously described (Doucette, et al., supra). The wire was advanced via the 3 Fr. infusion catheter positioned at the origin of the common iliac artery, to the proximal segment of the internal iliac artery supplying the ischemic limb. The Doppler wire records a real-time, spectral analysis of the Doppler signal, from which the average peak velocity (APV, the temporal average of the instanteous peak velocity waveform) is calculated and displayed on line. We required a stabilized velocity for 2 min before recording resting APV. Maximum APV was recorded after bolus injection of papaverine (Sigma, St. Louis, Mo.), 2 mg in 0.4 ml saline, via the infusion catheter. The Doppler wire was then pulled back from the internal iliac artery and readvanced to the common iliac artery of the normal limb; the distal tip of the 3 Fr. infusion catheter was repositioned at the origin of the common iliac artery. Blood flow velocity was again recorded at rest and after papaverine injection. After completing all Doppler measurements, the 3 Fr. infusion catheter was redirected to the promixal segment of the internal iliac artery of the ischemic limb, and selective internal iliac angiography was performed as described above.

Quantitative Analysis of Angiography and Flow Calculation. The angiographic luminal diameter of the internal iliac artery in the ischemic limb and of the external iliac artery in the normal limb were determined using an automated edge-detection system (Quantum 2000I; QCS, Ann Arbor, Mich.). The film selected for analysis was scanned with a high resolution video camera; the signal produced by the video camera was digitized and displayed on a video monitor (Laser Scan; ImageComm, Santa Clara, Calif.). Center-lines were traced manually for a 10-mm long segment beginning immediately distal to the tip of the Doppler wire. The contours were subsequently detected automatically on the basis of the weighted sum of first and second derivative functions applied to the digitized brightness information. The vascular diameter was then measured at the site of the Doppler sample volume (5 mm distal to the wire tip). Cross-sectional area was calculated assuming a circular lumen.

Doppler-derived flow was calculated as $Q_D=(\pi d^2/4)(0.5 \times APV)$ where $Q_D$=Doppler-derived time average flow, d=vessel diameter, and APV=time average of the spectral peak velocity. The mean velocity was estimated as 0.5×APV by assuming a time-averaged parabolic velocity profile across the vessel. The Doppler-derived flow calculated in this fashion has been shown to correlate with flow measurements determined by electromagnetic flow meters both in vitro and in vivo (Doucette, et al., supra). As 2 mg of papaverine had no effect on vessel diameter, we thus used the diameter measurements from the angiogram recorded immediately before the Doppler measurements for the calculation of both rest and maximum flow.

Regional Blood Flow to Limb Muscle. Regional tissue perfusion of animals with chronic hindlimb ischemia was determined using colored microspheres, 15 μm in diameter (Kowalik, *Circulation* 83, 974–82 (1991). After the completion of the invasive measurements described above, $3 \times 10^6$ of Dye-Trak colored microspheres (Triton Technology, Inc., San Diego, Calif.) were injected through a 3 Fr. Teflon catheter into the left ventricle via the common carotid artery. To collect blood samples for a reference flow, a second catheter was inserted into lower abdominal aorta via the common carotid artery and connected to a syringe withdrawal pump (Sage 351, Orion Research, Boston, Mass.). Through this catheter, the blood sample was withdrawn 10 sec prior to the microsphere injection over 3 min at a rate of 1.2 ml/min. The animals were then sacrificed and tissue samples (weight=2 g) of 2 different muscles (transfected medial thigh (adductor) muscle, and lower limb (gastrocnemius) muscle) of each hindlimb (ischemic and non-ischemic) were retrieved. The tissue samples and reference blood samples were digested with potassium hydroxide, following which microspheres were retrieved by vacuum filtering. After dyes were extracted from microspheres using dimethyl-formamide, the photometric absorption of each sample was determined using a conventional spectrophotometer (Model 8452A, Hewlett Packard, Palo Alto, Calif.) Regional blood flow to muscle was calculated as follows:

Tissue blood flow=(withdrawal rate/tissue weight)×(ODtissue/ ODreference blood), where OD=optical density.

VEGF Gene Expression in Skeletal Muscle

To evaluate expression of phVEGF$_{165}$ gene in skeletal muscle, sixteen additional male New Zealand white rabbits from both acute and chronic ischemia models (2 rabbits at each time point) were sacrificed at 3, 7, 14 and 30 days post-transfection. The presence of human VEGF mRNA was detected using reverse transcription-polymerase chain reaction (RT-PCR) as previously described (Takeshita, et al., *Proc Natl Acad Sci* (In press), supra). To ensure specificity and avoid amplification of endogenous rabbit VEGF, primers were selected from a region which is not conserved among different species. Sequences of primers used were: 5'-GAGGGCAGAATCATCACGAAGT-3' (sense)(SEQ ID NO:1); 5'-TCCTATGTGCTGGCCTTGGTGA-3' (antisense)(SEQ ID NO:2). RT-PCR products were analyzed by 2% agarose gel electrophoresis. DNA bands were visualized under UV illumination after staining with ethidium bromide.

Statistical analysis

Results were expressed as mean±standard deviation (SD). Statistical significance was evaluated using ANOVA followed by Scheffe's test. A value of $p<0.05$ was interpreted to denote statistical significance.

RESULTS

Anatomic Assessment

Figure 2B:
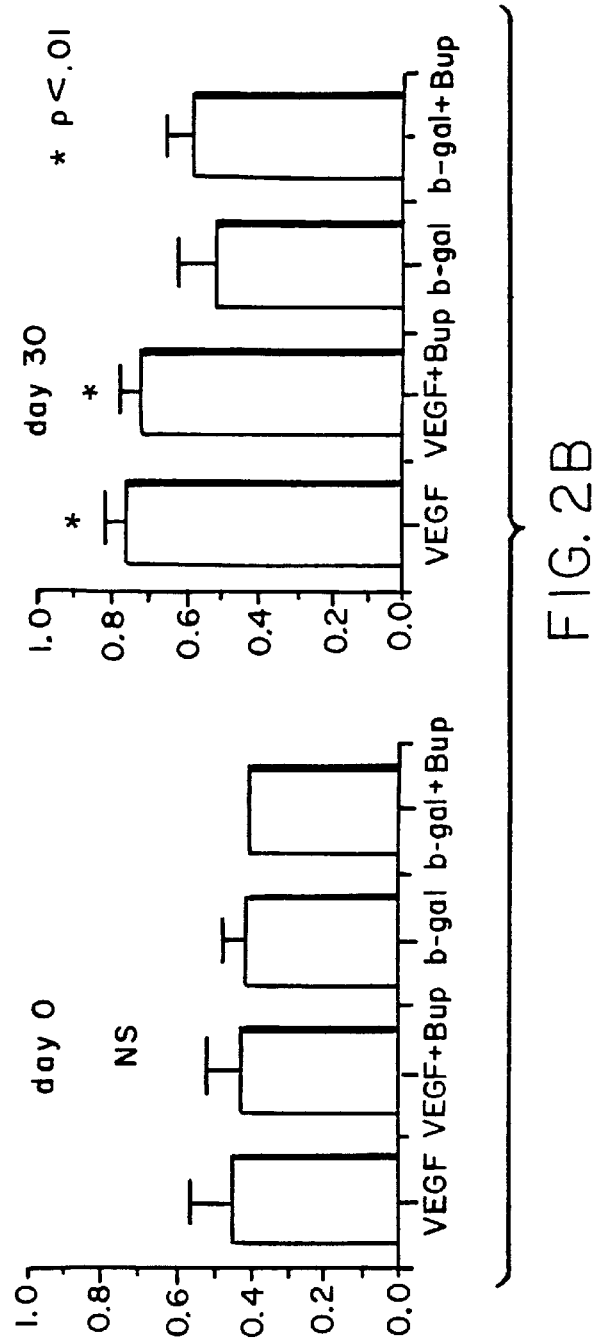

Angiography. Representative angiograms recorded from both control and VEGF-treated animals at day 30 are illustrated in FIG. 1. in control animals, collateral artery development in the medial thigh typically appeared unchanged or progressed only slightly in serial angiograms recorded at days 0 and 30. In contrast, in the VEGF-transfected group, marked progression of collateral artery was observed between days 0 and 30. As illustrated in FIG. 2, at baseline (day 0), there were no significant differences in angiographic score among groups (C I: 0.47±0.10, C II: 0.44±0.10, C III: 0.43±0.06, C IV: 0.42±0.10). By day 30, however, the angiographic score of each VEGF-transfected group was significantly improved compared to that of control (C I: 0.76±0.05, C II: 0.72±0.05, C III: 0.52±0.06, C IV: 0.58±0.09, p<0.01) as well as the acute model of limb ischemia (A I: 0.72±0.06, A II: 0.71±0.03, A III 0.48±0.10, p<0.01). Administration of bupivacaine had no observable effect.

Figures 3A, 3B:
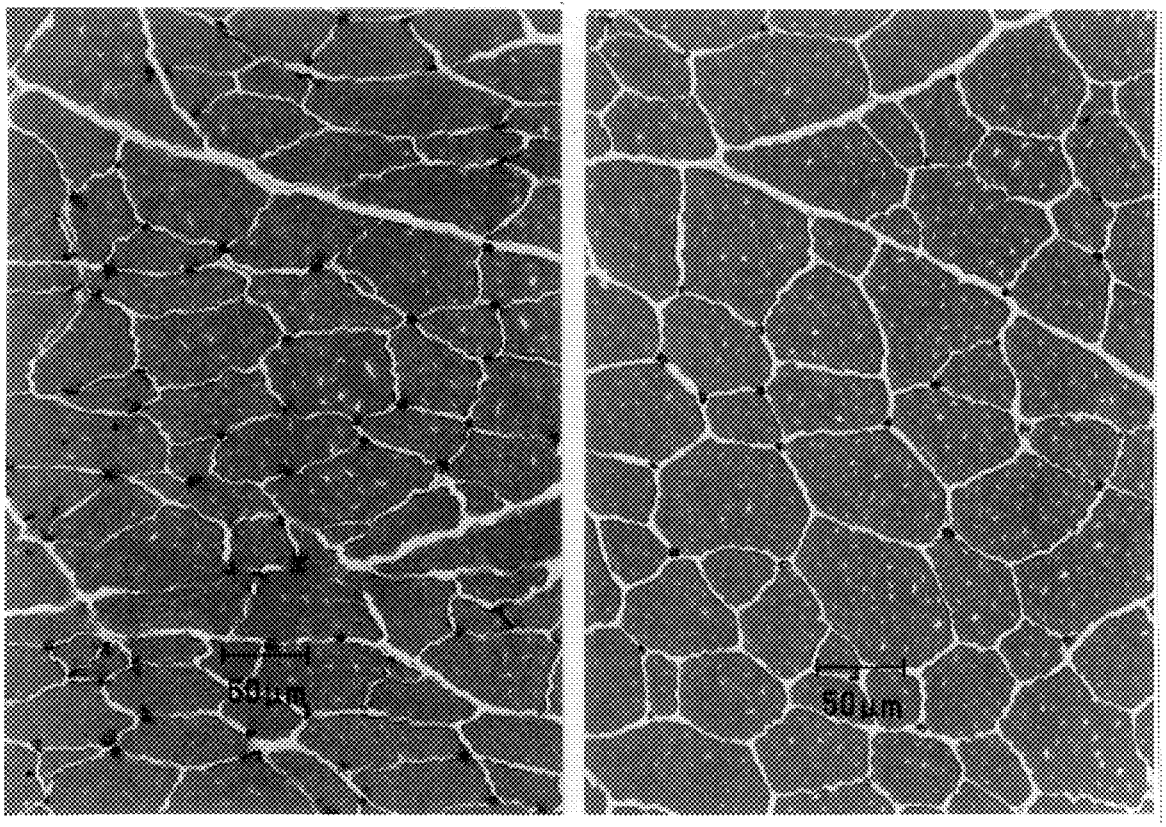
FIGS. 3A and 3B illustrates the favorable effect of intramuscular VEGF gene transfer upon revascularization at the capillary level (FIG. 3A VEGF, FIG. 3B control).
Figure 4A:
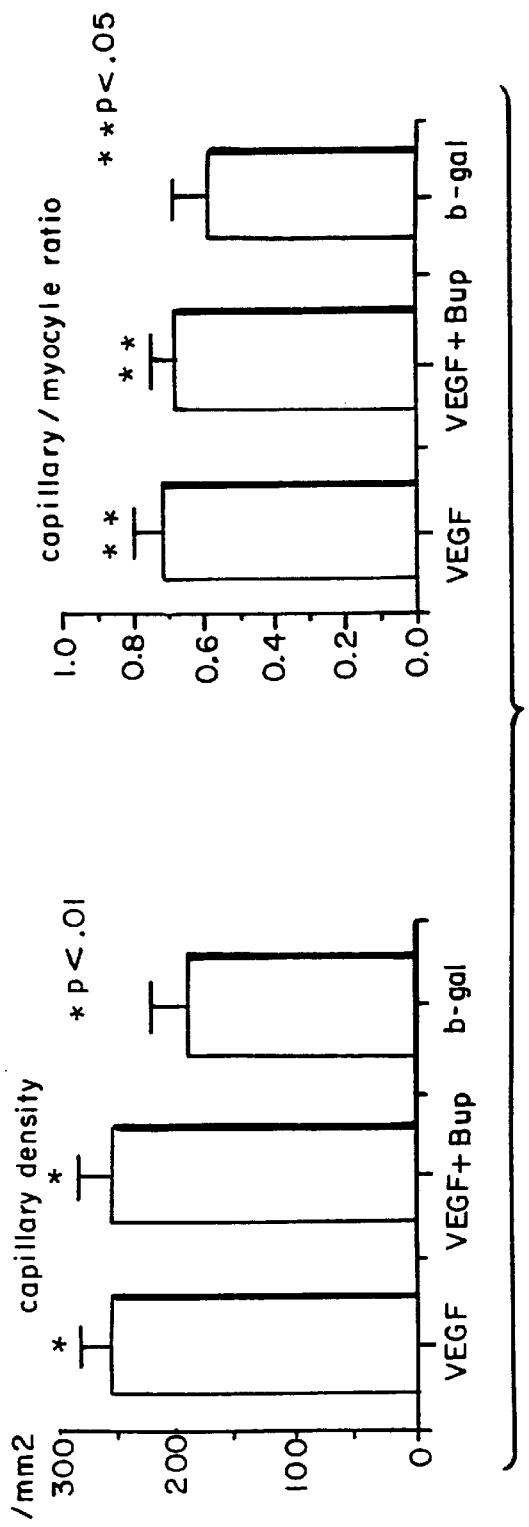
FIGS. 4A–4B illustrates capillary density and capillary/myocyte ratio in both the acute ischemia and chronic model of limb ischemia.
Figure 4B:
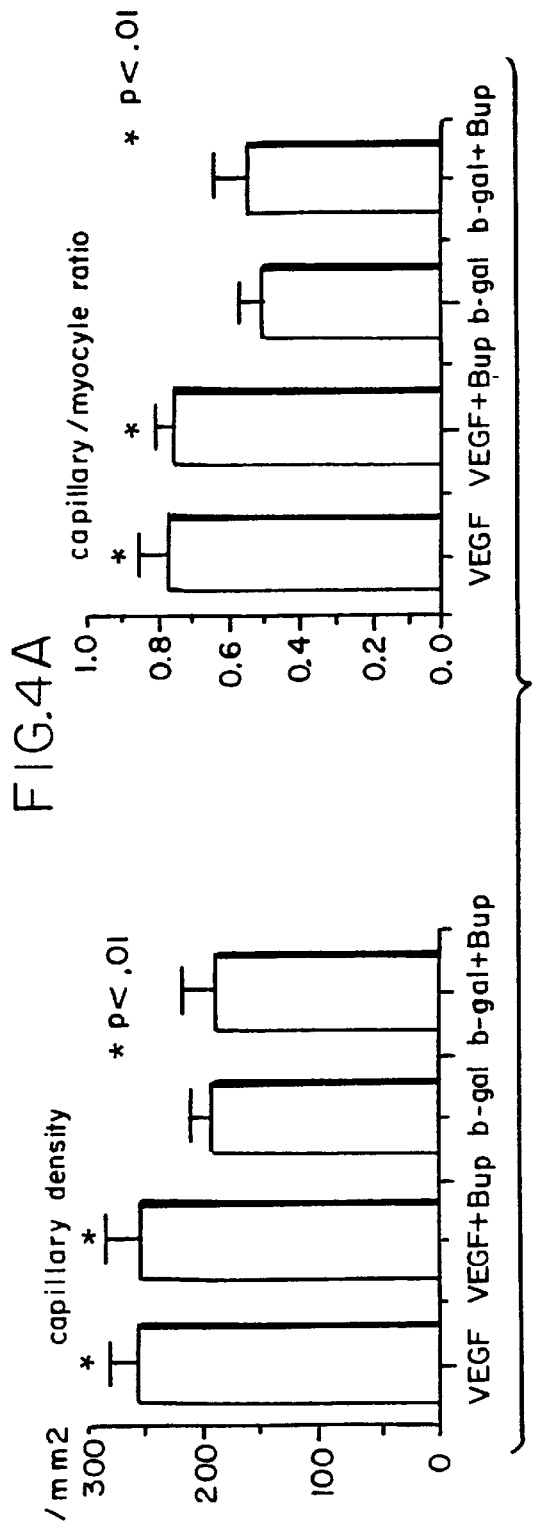

Capillary density and capillary/myocyte ratio. A favorable effect of intramuscular VEGF gene transfer upon revascularization was also apparent at the capillary level (FIGS. 3A and 3B). The adductor muscle of ischemic limbs was histologically examined at day 30 in both models. As illustrated in FIG. 4, VEGF-transfected animals had more capillaries around muscle fibers, in acute ischemia (A I: 248±37, A II: 228±22, A III: 188±32/mm$^2$, p<0.01) as well as the chronic model of limb ischemia (C I: 259±24, C II: 256±31, C III: 197±18, C IV: 192±31/mm$^2$, p<0.01). Analysis of capillary/myocyte ratio was also higher in VEGF-transfected animals in both the acute and chronic of hind-limb ischemia (acute model: A I: 0.73±0.07, A II: 0.70±0.06, A III: 0.61±0.09, p<0.01; chronic model: C I: 0.78±0.08, C II: 0.76±0.05, C III: 0.51±0.06, C IV: 0.55±0.09, p<0.01). No differences were observed between animals receiving bupivacaine versus those injected with saline.

Physiologic Assessment

Calf Blood Pressure. Reduction of the hemodynamic deficit in the ischemic limb following intramuscular VEGF-transfection was confirmed by measurement of calf blood pressure. As illustrated in FIG. 5, in animals with acute ischemia, the blood pressure ratio measured on day 30 post-transfection was significantly higher in VEGF-transfected groups than controls (A I: 0.80±0.09; A II: 0.76±0.11; A III: 0.56±0.10, p<0.01). There was no difference between bupivacaine and saline treated animals. In chronic model, 10 days after induction of ischemia (immediately prior to transfection), the calf blood pressure ratio was virtually identical in all groups (C I: 0.36±0.05; C II: 0.36±0.04; C III: 0.36±0.05; C IV: 0.32±0.03). By day 30 post-transfection, the blood pressure ratio for the VEGF-transfected groups was significantly higher than for the control (C I: 0.84±0.09; C II: 0.82±0.06; C III: 0.67±0.06; C IV: 0.66±0.10, p<0.01). There was no difference between bupivacaine and saline treated animals.

Intro-arterial Doppler guidewire measurement (Table 1). In acute ischemia model, VEGF-transfected animals revealed significantly higher flow to the ischemic limb at rest (A I: 21.6±5.2, A II: 19.5±3.2, A III: 13.9±3.7 ml/min. p<0.01) and at papaverine induced hyperemic status (A I: 59.1±16.9, A II: 55.2±5.1, A III: 39.0±11.5, ml/min, p<0.01). In chronic model, the rest blood flow to ischemic limb as well as papaverine stimulated flow to ischemic limb were identical in all groups at day 0 (rest flow; C I: 13.7±1.5; C II: 15.5±1.4; C III: 13.7±2.2; C IV: 13.4±1.9 ml/min, hyperemic flow; C I: 28.9±3.6, C II: 30.6±3.0, C III: 31.3±3.7, C IV: 28.1±1.7 ml/min). On day 30, VEGF transfected animals revealed significantly higher flow to the ischemic limb at rest (C I: 22.7±4.6, C II: 19.9±2.8, C III: 14.9±1.7, C IV: 14.1±1.5 ml/min, p<0.01) and at papaverine induced hyperemic status (C I: 52.5±12.6, C II: 56.0±12.0, C III: 38.4±4.3, C IV: 35.8±5.6 ml/min, p<0.05). The baseline and hyperemic flow to the non-ischemic limb was identical in all groups t day 0 as well as at day 30.

TABLE 1

Blood flow to ischemic limb

| | acute ischemia model | |
|---|---|---|
| | baseline | hyperemic |
| VEGF | 21.6 ± 5.2* | 59.1 ± 16.9* |
| VEGF + Bup | 19.5 ± 3.2* | 55.2 ± 5.1** |
| β-gal | 13.2 ± 3.7 | 39.0 ± 11.5 |
| β-gal + Bup | NA | NA |

| | chronic ischemia model | | | |
|---|---|---|---|---|
| | day 0 | | day 30 | |
| | baseline | hyperemic | baseline | hyperemic |
| VEGF | 13.7 ± 1.5 | 28.9 ± 3.6 | 22.7 ± 4.6* | 52.5 ± 12.6** |
| VEGF + Bup | 15.5 ± 1.4 | 30.6 ± 3.0 | 19.9 ± 2.8* | 56.0 ± 12.0** |
| β-gal | 13.7 ± 2.2 | 31.3 ± 3.7 | 14.9 ± 1.7 | 38.4 ± 4.3 |
| β-gal + Bup | 13.4 ± 1.9 | 28.1 ± 1.7 | 14.1 ± 1.5 | 35.8 ± 5.6 | values are described as means ± SD (ml/min)
*P < 0.1, **p < .05 vs β-gal or β-gal + Bup by ANOVA Regional Blood Flow to Limb Muscle (Table 2). Regional blood flow to ischemic limb muscles was analyzed using colored microsphere technique in chronic ischemia model. Regional blood flow at adductor muscle, transfected medial thigh muscle (C I: 4.3±0.5, C II: 4.6±1.2, C III: 2.9±0.6, C IV: 3.1±0.4 ml/min/100 g tissue, p<0.05), as well as distal lower limb muscle, gastrocnemius (C I: 3.9±0.8, C II: 4.2±0.7, C III: 2.8±0.9, C IV: 2.6±0.7, ml/min/100 g tissue, p<0.05) was 1.5 folds greater in VEGF transfected animals. No significant differences owing to injected solution were observed. There were no differences in the regional flow to the non-ischemic muscles in all groups (flow to adductor: C I: 5.2±0.5, C II: 5.6±1.0, C III: 4.9±0.6, C IV: 5.6±1.0 ml/min/100 g tissue, flow to gastrocnemius: C I: 4.4±1.0, C II: 4.7±1.0; C III: 4.6±1.2, C IV: 5.0±1.1 ml/min/100 g tissue).

TABLE 2

Regional blood flow to limb muscle

| | chronic ischemia model | | | |
|---|---|---|---|---|
| | adductor | | gastrocnemius | |
| | ischemic | normal | ischemic | normal |
| VEGF | 4.3 ± 0.5* | 5.2 ± 0.5 | 3.9 ± 0.8* | 4.4 ± 1.0 |
| VEGF + Bup | 4.6 ± 1.2* | 5.6 ± 1.0 | 4.2 ± 0.7* | 4.7 ± 1.0 |
| β-gal | 2.9 ± 0.6 | 4.9 ± 0.6 | 2.8 ± 0.9 | 4.6 ± 1.2 |
| β-gal + Bup | 3.1 ± 0.4 | 5.6 ± 1.0 | 2.6 ± 0.7 | 5.0 ± 1.1 | values are described as means ± SD (ml/min/100 g tissue)
*p < 0.5 vs. β-gal or β-gal + Bup by ANOVA

Human VEGF Gene Expression in Muscle

Figure 6:
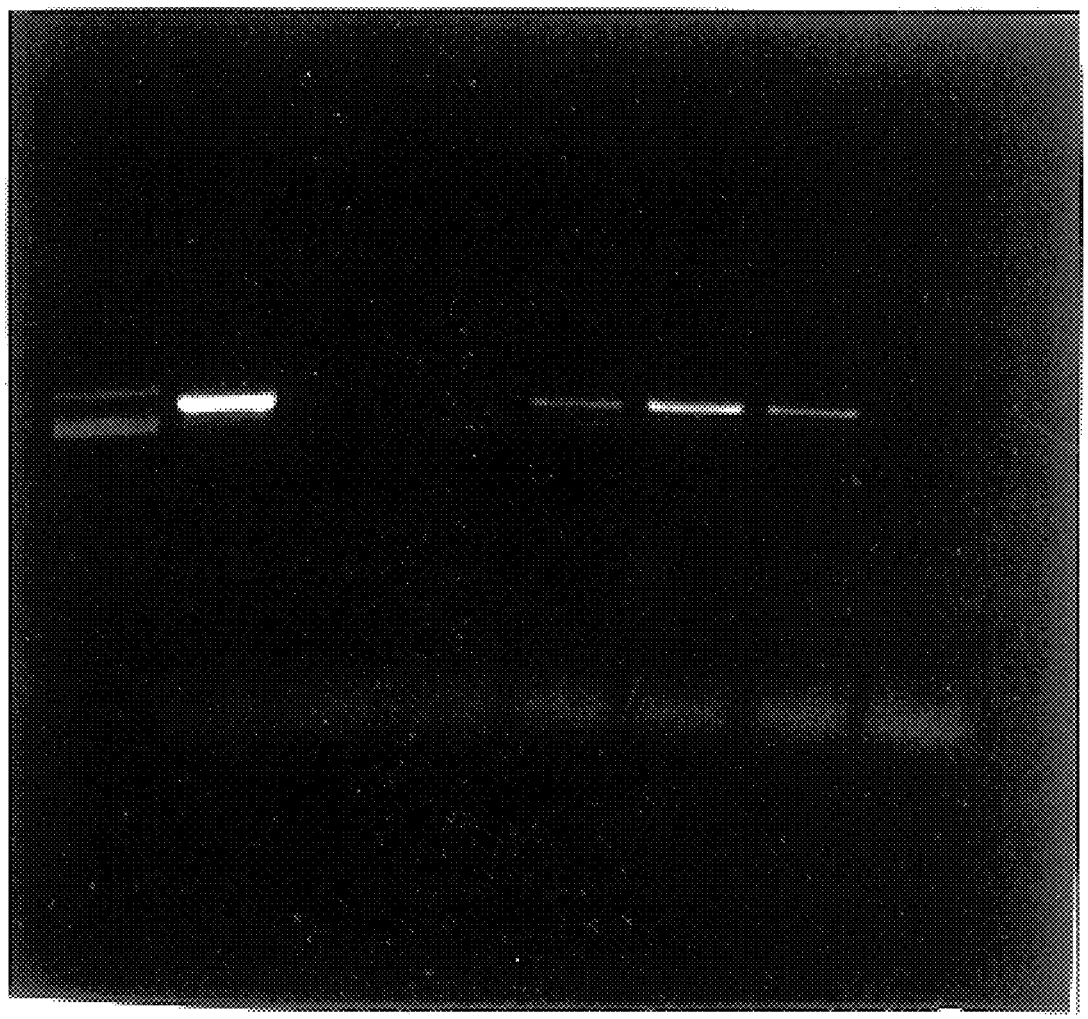
FIG. 6 illustrates the time course of VEGF expression. Lane 1: marker, Lane 2: positive control, Lane 3: nontransfected muscle, Lane 4: on RT, Lanes 5, 6, 7 and 8 are 3, 7, 14 and 30 days after transfection, respectively.

To confirm expression of human VEGF gene in transfected rabbit limb muscle in vivo, we analyzed transfected arteries for the presence of human VEGF mRNA by RT-PCR. As indicated above, to ensure the specificity of RT-PCR for human VEGF mRNA resulting from successful transfection (versus endogenous rabbit VEGF mRNA), primers employed were selected from a region which is not conserved among different specie. Adductor muscles were harvested 3, 7, 14 and 30 days after VEGF gene injection. The presence of human VEGF mRNA was readily detected adductor muscles with phVEGF$_{165}$ from day 3 to day 14 in both acute and chronic models. Rabbit adductor muscles injected with pGSVLacZ gene were negative for human VEGF mRNA (FIG. 6).

We have demonstrated that a gene encoding an angiogenic protein can be successfully transferred into ischemic muscle where the gene is expressed and induces angiogenesis, providing the ischemic tissue with an increase in blood vessels.

What is claimed is:

1. A method for inducing the formation of new blood vessels in an ischemic muscle tissue in a human host, comprising:
    (a) selecting a human host in need of increased blood flow in an ischemic muscle tissue, and
    (b) directly injecting into said tissue of said human host an effective amount of a DNA sequence encoding an angiogenic protein or a modified angiogenic protein, wherein said DNA sequence comprises a promoter sequence and either a native secretory signal sequence or an operably linked secretory signal sequence, wherein the angiogenic protein or modified angiogenic protein is selected from the group consisting of acidic and basic fibroblast growth factors, vascular endothelial growth factor, endothelial cell growth factor, epidermal growth factor, transforming growth factor α and β, platelet-derived endothelial growth factor, platelet-derived growth factor, tumor necrosis factor α, hepatocyte growth factor, and insulin-like growth factor, and wherein said effective amount of said DNA sequence expresses sufficient angiogenic protein in said tissue to induce new blood vessel formation in said human host.

2. The method of claim 1, wherein said angiogenic protein is vascular endothelial growth factor.

3. The method of claim 1, wherein said angiogenic protein is acidic fibroblast growth factor.

4. The method of claim 1 wherein the angiogenic protein is an endothelial growth factor.

5. The method of claim 1 wherein the DNA encoding the angiogenic protein has been modified to contain an operably linked secretory signal sequence.

6. The method of claim 1, wherein 500 µg of the DNA is injected into the tissue.

7. The method of claim 1, wherein the amount of the DNA injected into the tissue is between about 1,000 µg and 2,000 µg.

8. The method of claim 1, wherein the amount of the DNA injected into the tissue is between about 2,000 µg and 4,000 µg.

9. The method of claim 1, wherein a volume of about 2.5 ml of the DNA in a pharmaceutically acceptable carrier is injected into the tissue.

10. The method of claim 1, wherein the DNA is injected in a series of injections into the tissue.

11. The method of claim 1, wherein angiographic analysis shows substantial improvement of the angiographic score for the treated tissue within 30 days after treatment.

12. The method of claim 1, wherein the treated tissue shows substantial improvement in capillary to myocyte ratio within 30 days after treatment.

13. The method of claim 1, wherein the treated tissue shows substantial improvement in blood pressure within 30 days after treatment.

14. The method of claim 1, wherein the treated tissue shows substantial improvement in blood flow within 30 days after treatment.

15. The method of claim 1, wherein the injected DNA is operatively linked to a cytomegalovirus promoter.

16. A method for inducing the formation of new blood vessels in ischemic limb muscle tissue in a human host, comprising:
    (a) selecting a human host in need of increased blood flow in ischemic limb muscle tissue, and
    (b) directly injecting into said tissue of said human host an effective amount of a DNA sequence encoding an angiogenic protein or a modified angiogenic protein, wherein said DNA sequence comprises a promoter sequence and either a native secretory signal sequence or an operably linked secretory signal sequence, said DNA sequence being free of an adenoviral vector, wherein the angiogenic protein or modified angiogenic protein is selected from the group consisting of acidic and basic fibroblast growth factors, vascular endothelial growth factor, endothelial cell growth factor, epidermal growth factor, transforming growth factor α and β, platelet-derived endothelial growth factor, platelet-derived growth factor, tumor necrosis factor α, hepatocyte growth factor, and insulin-like growth factor, and wherein said effective amount of said DNA sequence expresses sufficient angiogenic protein in said tissue to induce new blood vessel formation in said human host.

17. The method of claim 16, wherein said angiogenic protein is vascular endothelial growth factor.

18. The method of claim 16, wherein said angiogenic protein is acidic fibroblast growth factor.

19. The method of claim 16, wherein the angiogenic protein is an endothelial growth factor.

20. The method of claim 16, wherein the DNA encoding the angiogenic protein has been modified to contain an operably linked secretory signal sequence.

21. The method of claim 16, wherein 500 µg of the DNA is injected into the tissue.

22. The method of claim 16, wherein the amount of the DNA injected into the tissue is between about 1000 µg and 2,000 µg.

23. The method of claim 16, wherein the amount of the DNA injected into the tissue is between about 2,000 µg and 4,000 µg.

24. The method of claim 16, wherein a volume of about 2.5 ml of the DNA in a pharmaceutically acceptable carrier is injected into the tissue.

25. The method of claim 16, wherein the DNA is injected in a series of injections into the tissue.

26. The method of claim 16, wherein angiographic analysis shows substantial improvement of the angiographic score for the treated tissue within 30 days after treatment.

27. The method of claim 16, wherein the treated tissue shows substantial improvement in capillary to myocyte ratio within 30 days after treatment.

28. The method of claim 16, wherein the treated tissue shows substantial improvement in blood pressure within 30 days after treatment.

29. The method of claim 16, wherein the treated tissue shows substantial improvement in blood flow within 30 days after treatment.

30. The method of claim 16, wherein the injected DNA is operatively linked to a cytomegalovirus promoter.

* * * * *